United States Patent
Weber

(10) Patent No.: US 6,470,506 B2
(45) Date of Patent: Oct. 29, 2002

(54) PORTABLE AND SELF-OPERABLE PERINEAL DEVICE

(76) Inventor: William A. Weber, 1138 Brownsville Rd., Pittsburgh, PA (US) 15210

( * ) Notice: Subject to any disclaimer, the term of this patent is extended or adjusted under 35 U.S.C. 154(b) by 0 days.

(21) Appl. No.: 09/811,009

(22) Filed: Mar. 16, 2001

(65) Prior Publication Data

US 2002/0129442 A1 Sep. 19, 2002

(51) Int. Cl.[7] .................................................. E03D 9/08
(52) U.S. Cl. ...................................................... 4/420.1
(58) Field of Search ............................. 4/420.1–420.5, 4/443–448; 239/437, 438, 443

(56) References Cited

U.S. PATENT DOCUMENTS

| | | | | |
|---|---|---|---|---|
| 2,705,495 A | * | 4/1955 | Vrana et al. | 4/420.1 |
| 3,377,629 A | * | 4/1968 | DiPasquale | 4/445 |
| 3,430,268 A | * | 3/1969 | Zoberg | 4/420.1 |
| 4,000,742 A | * | 1/1977 | DiGiacomo | 4/420.1 |
| 5,165,456 A | * | 11/1992 | Woolman | 141/98 |
| 5,277,805 A | * | 1/1994 | Ferguson | 210/266 |

* cited by examiner

Primary Examiner—Charles R. Eloshway
(74) Attorney, Agent, or Firm—William F. Hamrock PA

(57) ABSTRACT

An individually operable and portable perineal device for cleaning and medicating the rectal and vaginal areas of the human body. The device is releasably mounted on a standard bathroom water faucet by means of a two-way water outlet valve converter attachment having an outlet into the sink and an alternate outlet into plastic tubing. The tubing directs the flow of water into either a catheter designed for cleaning and medicating the rectal cavity or into a catheter for cleaning and medicating the vaginal cavity. The device is operable manually by an individual user while seated on a toilet without the assistance of another person. The device ia packageable in a small package or traveling kit and can easily cleaned in a bathroom sink after use.

11 Claims, 3 Drawing Sheets

PORTABLE AND SELF-OPERABLE PERINEAL DEVICE

BACKGROUND OF THE INVENTION

The present invention relates to a small lightweight, portable device releasably attachable to a water faucet for supplying a stream of water or liquid for perineal cleaning and medicating the rectal and vaginal areas of the human body.

There are many types of cleaning and hygienic devices known for cleaning the perineal area of the human body. When using a large number of these devices, the user requires the assistance of another person, in particular, when the user is sick and/or bedridden, and/or must be moved to a toilet, when performing the cleaning activity. In these and other situations, and especial when the user is an elderly woman, the user quite often feels that the presence of the other person is an invasion of one's privacy. This can result in embarrassment, self-consciousness, distress, shame, humiliation and mortification. Clearly, a more dignified, discreet and private manner of performing the cleaning activity would be definitely desirable. This is especially true in those situations wherein the user has to be assisted to the toilet while conducting the cleaning activity.

Further, with respect to these prior art perineal cleaning devices, many of these devices are very limited in their cleaning capabilities being directed to cleaning only specific perineal area. and cannot be used for cleaning both the rectal and vaginal areas of the human body. Also, many of these known devices require that they be permanently installed to a water system and/or to a toilet. Furthermore, many of these devices have complicated mechanisms which are difficult to use and cannot be operated by an individual user without the assistance of another person. Furthermore, many of these devices are difficult to clean resulting in a messy cleaning operation after use.

In light of the many disadvantages and difficulties with these known perineal cleaning devices, there is a need for a small, lightweight, portable, packageable device which is not only releasably attachable to a standard bathroom water faucet for supplying a stream of water or liquid for cleaning and medicating, not only one area, but both the rectal and vaginal cavity areas of the human body. Further needs are satisfied if it is easy to use individually by the user without assistance, can be easily cleaned, can be permanently attached to the water faucet or can be detached and stored in a small lightweight package which can be carried about.

SUMMARY OF THE INVENTION

The present invention overcomes many of the deficiencies of the known perineal cleaning devices. Accordingly the present invention provides a small, lightweight, portable rectal and vaginal cleaning device which is safe and easy to use, and can be used privately and unassisted by the individual user. It does not require plumbing operations to be installed since it is releasably attachable to a standard bathroom water faucet outlet. It can be easily cleaned and stored out of sight, and can be carried in a small package when traveling.

The present rectal and vaginal cleaning device comprises an elongated, flexible plastic tubing, one end of which is adapted for fluid communication with a standard bathroom water faucet outlet through a small two-way water outlet valve converter attachment releasably attached to the faucet outlet. The opposite end of the plastic tubing is adapted for releasably connection either to an individual plastic catheter designed for cleaning and medicating the user's rectal cavity or to a separate plastic catheter designed for cleaning and medicating the user's vaginal cavity.

When using the present device, the user removes the standard threaded filter attachment to the conventional faucet outlet and replaces it with the present two-way water outlet valve converter attachment. If the plastic tubing is not in place, one end of the tubing is releasably secured to the valve converter attachment outlet and the opposite end of the tubing is releasably secured to the particular catheter to be used. The user is then able to turn the handle of the valve converter attachment by hand and regulate the flow of water through the device while seated on the toilet seat.

BRIEF DESCRIPTION OF THE DRAWINGS

This invention is described by appended claims in relation description of preferred embodiments with reference to the following drawings which are described briefly as follows:

DESCRIPTION OF THE PREFERRED EMBODIMENTS

Terms used to describe features of this invention are listed below with numbering in the order of their initial use with reference to the drawings. These terms and the numbers assigned to them designate the same features wherever used throughout this description.

Figure 1:
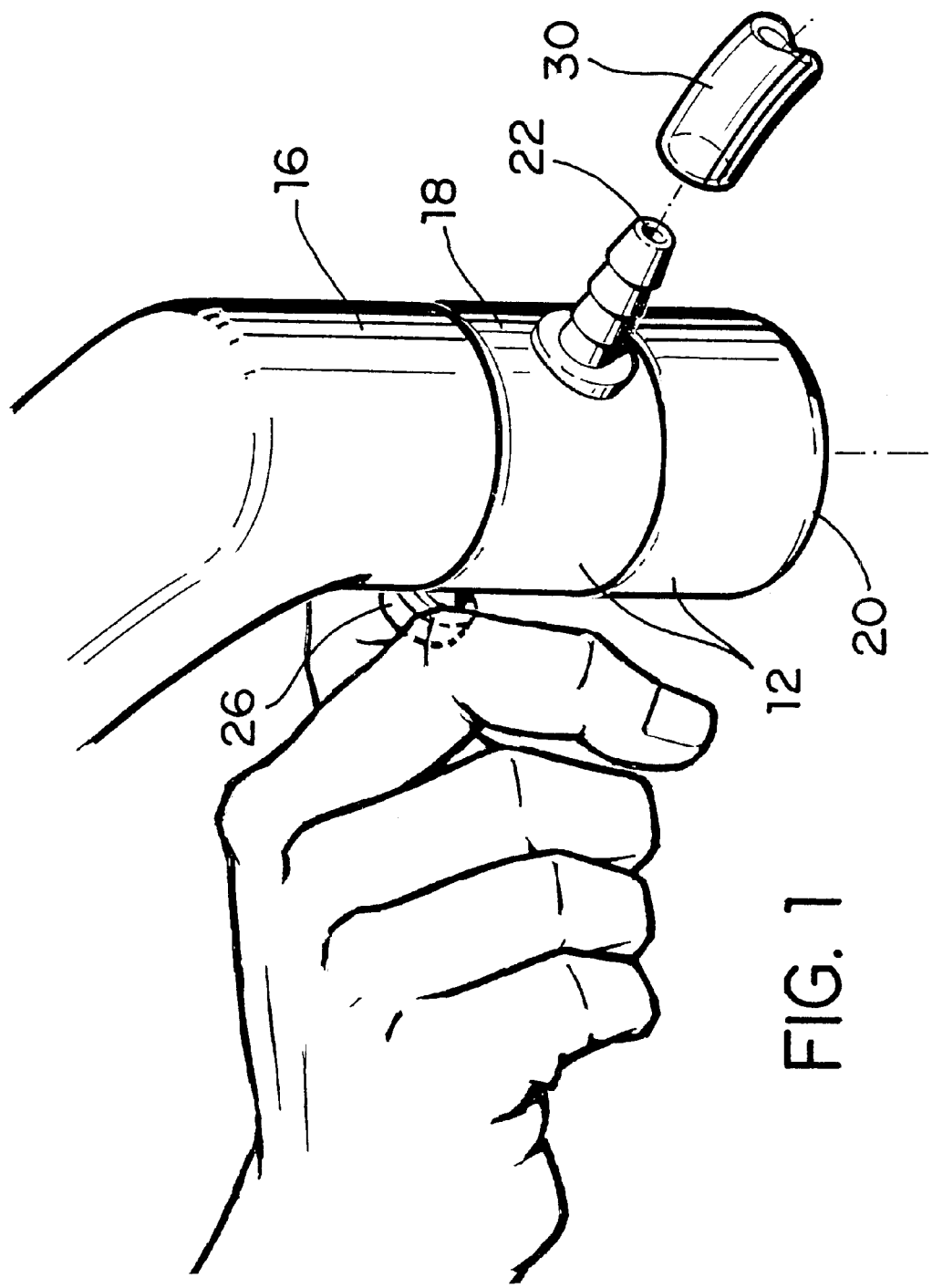
FIG. 1 is an isometric view of the device of the invention mounted on a standard water faucet outlet.
Figure 2:
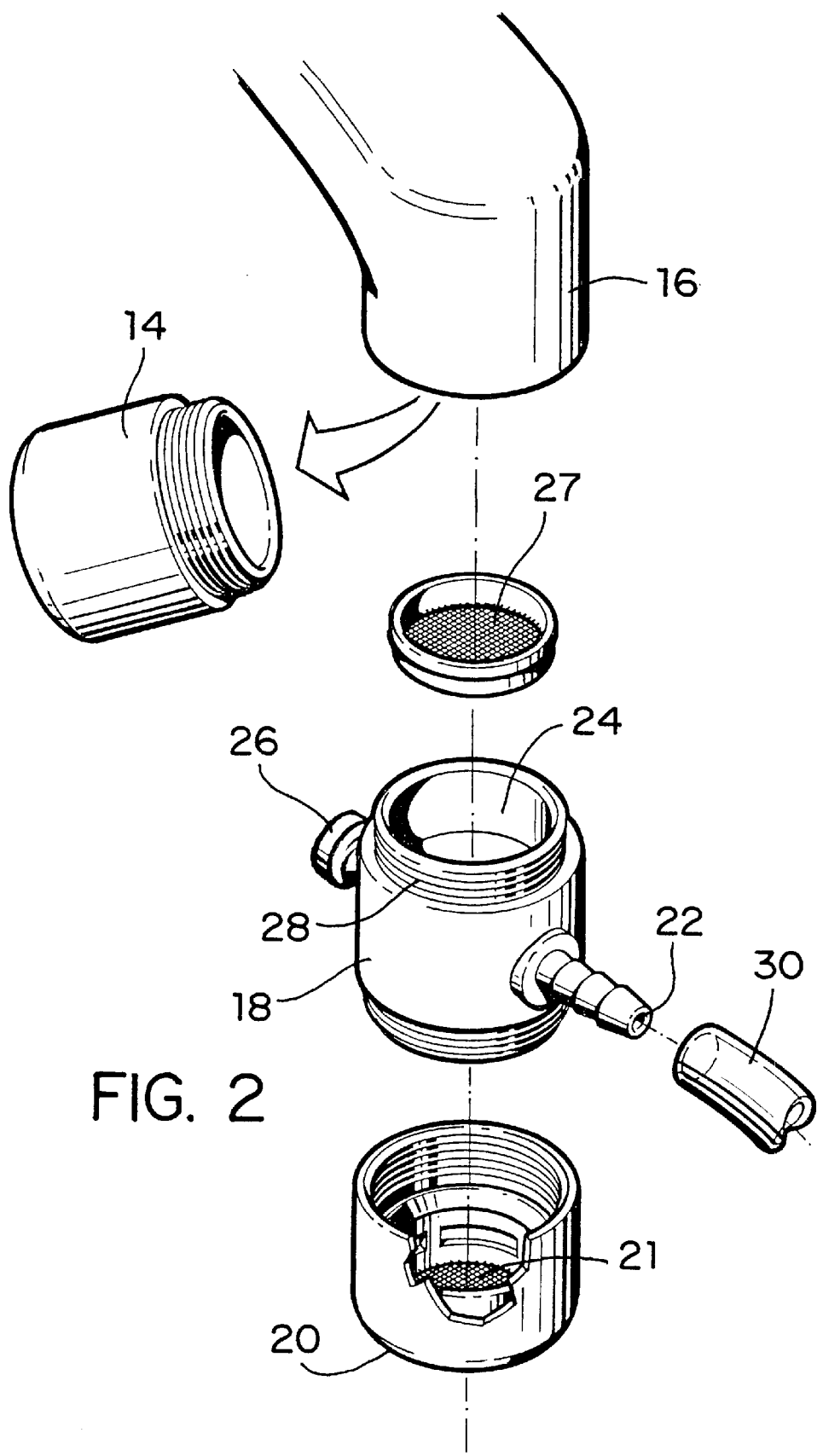
FIG. 2 is an isometric exploded view of the two-way valve converter attachment releasably attachable to the water faucet and the flexible tubing.
Figure 3:
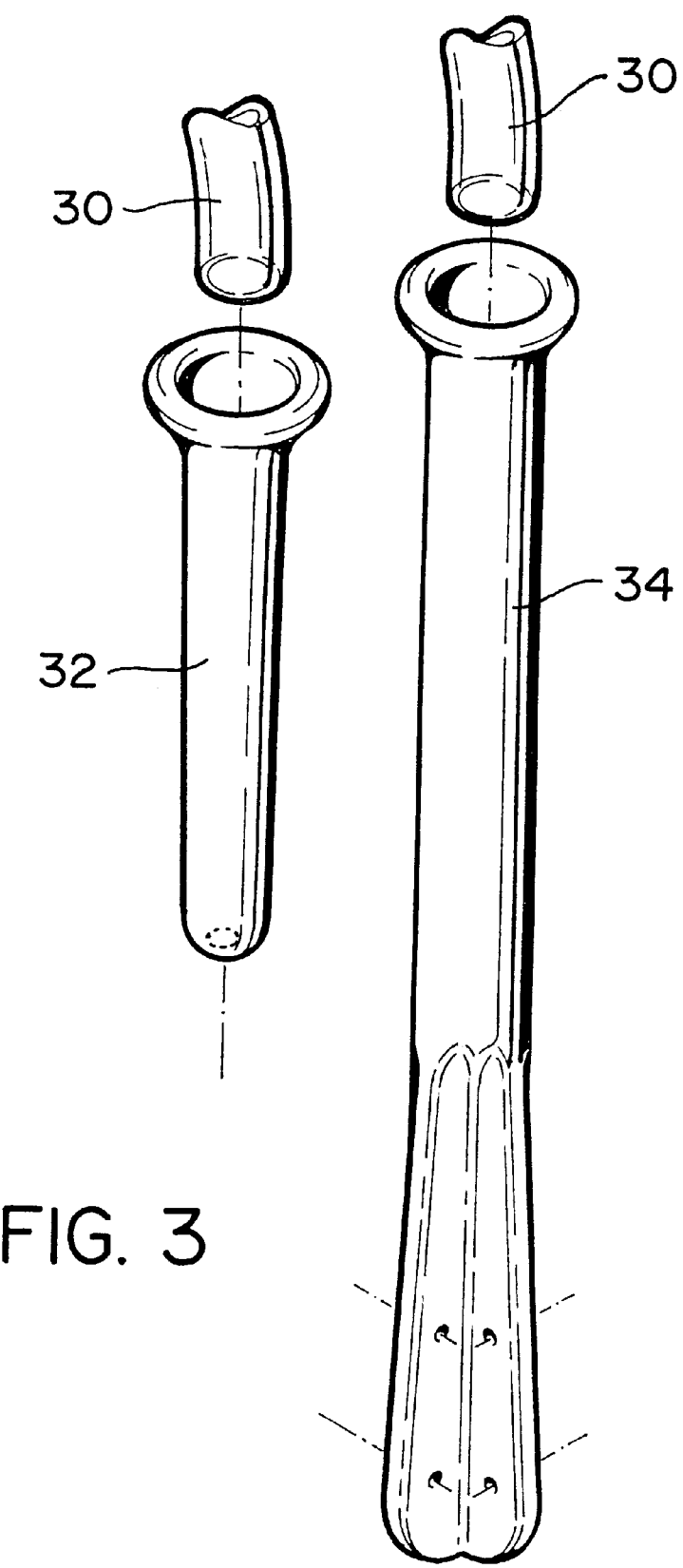
FIG. 3 is an isometric sectional of the opposite end of the flexible tubing attachable to the catheters.

Referring now to the drawings, FIG. 1 is an illustrative view of the perineal cleaning device for cleaning and medicating the vaginal and rectal cavities of the human body in accordance with the present invention. The device comprises a small cylindrical two-way outlet valve converter attachment 12 as depicted in FIG. 2 which regulates and directs the flow of water through the device. Two-way valve converter attachment 12 attaches to the water supply by replacing the standard bathroom water faucet outlet filter attachment 14 which is generally releasably attached to almost all standard water faucet outlets 16 by means of threaded engagement. Valve converter attachment 12 is comprised of cylindrical valve body 18 provided with two outlet ports, numeral 20 located at the base of the converter attachment and numeral 22 located on the side of the converter attachment and two filter attachments 21 and 27. Each of these converter attachments' outlet ports receives its individual flow of water through inlet port 24 by means of handle 26 regulating and directing the flow of water into one or the other of outlet ports 20 or 22 whichever is operating in the open position. When outlet port 22 is operating in the open position, outlet port 20 is in the closed position, and the entire water flow is directed into plastic tubing connected to outlet port 22. When outlet port 20 is operating in the open position, outlet port 22 is in the closed position, and the entire flow of water is directed into the bathroom sink. Externally threaded annular connector 28 of inlet port 24 releasably connects valve converter attachment 12 to the internally threaded water faucet outlet 16. Flexible elongated plastic tubing 30 transports the flow of water from the valve converter to one of two catheters. The elongated plastic tubing is very flexible and resilient and is releasably connected at one end to outlet port 22 and is releasably attached at its opposite end to either rectal cavity cleaning catheter 32 or vaginal cavity cleaning catheter 34 as depicted in FIG. 3. Each end of the plastic tubing is frictionally connected, or secured by other known means, to outlet port 22 and to each catheter. The tubing can be any length that will comfortably meet the requirements of the user. Generally, when the toilet is located in close proximity or adjacent to the sink and/or water faucet, elongated flexible tubing 30 is about four to six feet in length.

In use, initially, the standard outlet filter attachment 14 is removed from water faucet outlet 16. Two-way valve converter attachment 12 is releasably mounted to the faucet outlet by engaging externally threaded connector 28 within internally threaded faucet outlet 16. Other known connecting means to the faucet outlet if it externally threaded or not threaded are permissible Since two-way valve converter attachment 12 regulates the water flow through either outlet port 20 or 22 by means of handle 26, an alternative embodiment of the invention allows the valve converter attachment to be permanently attached to the faucet outlet directing the water flow through outlet port 20 into the sink. When it becomes necessary to use the present device for perineal cleaning, the elongated flexible tubing can be connected to outlet port 22 to direct the water flow to the required catheter. Usually, the user is able to manually operate the device while positioned on the toilet seat by operating handle 26 by hand; this is especially so when the toilet is adjacent to the water faucet and sink.

Another embodiment of the invention permits carrying the entire device in a small package and applying it to a standard bathroom faucet when the user is traveling. The fact that the device is so small and has so few parts, the parts can be easily cleaned in a bathroom sink and quickly repackaged.

Another further embodiment of the invention permits medication to be added to the valve converter attachment or the catheters to be administered to the user in the water flow. This is an important feature when medication must be included in the treatment.

Thus, it will be appreciated that as a result of the present invention, a highly effective perineal device for cleaning and medicating the vaginal and rectal areas of the human body by which the requirements of the present invention are completely fulfilled. It is to be understood, however, that modifications and/or changes may be made in the disclosed embodiments without departure from the present invention. Accordingly it is to be expressly understood that the foregoing description and accompanying drawings are representative of preferred embodiments only, not limiting, and that the true spirit and scope of the present invention are to be determined by reference to the appended claims.

What is claimed is:

1. A device for perineal cleaning and medicating the human body comprising:
    a two-way outlet valve attachment comprising a main body section defining a water inlet port that is releasably attachable to a water faucet outlet and a lower body section attachable to the main body section, the lower body section defining a first water outlet port and the main body section defining an alternate water outlet port;
    first and second filters, the first filter interposed between the main body section and the water faucet, the second filter interposed between the main body section and the lower body section;
    a flexible tubing having a front end and an opposite end, the front end of the tubing attachable to the alternate water outlet port; and
    a perineal cleaning and medicating attachment attachable to the opposite end of the flexible tubing.

2. The device according to claim 1 wherein the cleaning and medicating attachment is designed for cleaning and medicating the rectal cavity.

3. The device according to claim 1 wherein the cleaning and medicating attachment is designed for cleaning and medicating the vaginal cavity.

4. The device according to claim 1 wherein the cleaning and medicating attachment is a hand-held device operable by the user.

5. The device according to claim 4 wherein the first water outlet port directs the flow of water away from the alternate water outlet port.

6. The device according to claim 5 wherein the alternate water outlet port directs the flow of water into the flexible tubing.

7. The device according to claim 6 wherein the flexible tubing is made of resilient material and is about ten feet in length.

8. The device according to claim 7 wherein the flexible tubing is-about six feet in length.

9. The device according to claim 8 wherein the two-way outlet valve attachment is threadably mountable on the water faucet.

10. The device according to claim 9 wherein the flexible tubing is frictionally mounted on the alternate water outlet port and the cleaning and medicating attachment.

11. The device according to claim 9 wherein the two-way outlet valve attachment further includes a handle for directing water through the first and alternate outlet ports.

* * * * *